(12) United States Patent
Lugade et al.

(10) Patent No.: US 7,504,089 B2
(45) Date of Patent: *Mar. 17, 2009

(54) CYANINE DYES

(75) Inventors: Ananda G. Lugade, Austin, TX (US); Narasimhachari Narayanan, Wilmington, MA (US); Daniel R. Draney, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/267,643

(22) Filed: Nov. 4, 2005

(65) Prior Publication Data

US 2006/0063247 A1 Mar. 23, 2006

Related U.S. Application Data

(60) Division of application No. 10/354,812, filed on Jan. 28, 2003, now Pat. No. 6,995,274, which is a continuation of application No. PCT/US01/29385, filed on Sep. 18, 2001.

(60) Provisional application No. 60/233,511, filed on Sep. 19, 2000.

(51) Int. Cl.
*A61B 10/00* (2006.01)
*A61B 5/00* (2006.01)
*A61B 8/00* (2006.01)

(52) U.S. Cl. .................. 424/9.6; 424/1.11; 424/1.49; 424/1.69; 424/1.73; 424/1.65; 548/427

(58) Field of Classification Search .................. 548/427, 548/455; 424/1.11, 1.65, 9.6, 1.69, 1.73; 530/300, 387.1; 536/322, 1.11; 514/773, 514/836

See application file for complete search history.

(56) References Cited

U.S. PATENT DOCUMENTS

| | | | |
|---|---|---|---|
| 5,268,486 A | | 12/1993 | Waggoner et al. |
| 5,519,145 A | * | 5/1996 | Fabricius et al. ............ 548/450 |
| 5,536,626 A | * | 7/1996 | Fabricius et al. ............ 430/522 |
| 5,556,959 A | | 9/1996 | Brush et al. |
| 5,571,388 A | | 11/1996 | Patonay et al. |
| 6,083,485 A | * | 7/2000 | Licha et al. .................. 424/9.6 |
| 6,498,945 B1 | * | 12/2002 | Alfheim et al. ............ 600/407 |
| 6,641,798 B2 | | 11/2003 | Achilefu et al. |
| 6,642,375 B2 | | 11/2003 | Inomata et al. |
| 6,649,335 B2 | | 11/2003 | Missfeldt |
| 6,747,159 B2 | | 6/2004 | Caputo et al. |
| 6,995,274 B2 | * | 2/2006 | Lugade et al. ............... 548/427 |

2004/0014981 A1 1/2004 Lugade et al.

FOREIGN PATENT DOCUMENTS

| | | |
|---|---|---|
| CA | 2145405 | 2/1995 |
| DE | 43 26 466 | 2/1995 |
| EP | 0 580 145 A2 | 1/1994 |
| EP | 0 580 145 A3 | 1/1994 |
| EP | 580145 | 1/1994 |
| JP | 6-145539 | 5/1994 |
| JP | 6-145539 A | 5/1994 |
| WO | WO 97/13810 A1 | 4/1997 |
| WO | WO 98/52609 A1 | 11/1998 |
| WO | WO 99/05221 A1 | 2/1999 |
| WO | WO 00/16810 A1 | 3/2000 |
| WO | WO 2007/005222 A2 | 1/2007 |
| WO | WO 2007/005222 A3 | 1/2007 |

OTHER PUBLICATIONS

Narayanan, N., et al., A New Method For the Synthesis of Heptamethine Cyanine Dyes: Synthesis of New Near Infrared Fluorescent Labels, Journal of Organic Chemistry, American Chemical Society, 1995, pp. 2391-2395, vol. 60, XP 002065376, ISSN: 0022-3263.

International Search Report for PCT/US01/29385, dated Feb. 25, 2002.

* cited by examiner

*Primary Examiner*—D. L Jones
(74) *Attorney, Agent, or Firm*—Townsend and Townsend and Crew LLP

(57) ABSTRACT

A compound of the formula (I)

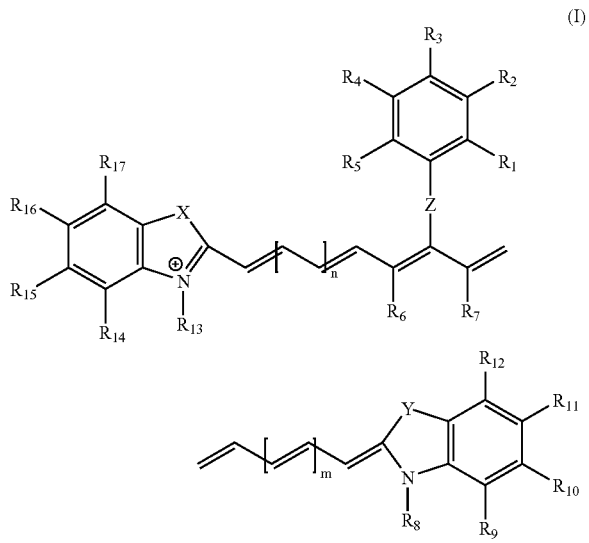

wherein the variables are defined herein. Methods of dye-labeling biomolecules with the compound of formula (I) and dye-labeled biomolecules are also provided.

34 Claims, No Drawings

CYANINE DYES

RELATED APPLICATIONS

The present application is a divisional application of U.S. patent application Ser. No. 10/354,812, allowed, which application is a continuation of PCT application Ser. No. US01/29385 filed on Sep. 18, 2001, which application claims the benefit under 35 U.S.C. § 119(e) of the filing date of the provisional U.S. patent application having Ser. No. 60/233,511, filed on Sep. 19, 2000, which are all hereby incorporated by reference.

FEDERALLY SPONSORED RESEARCH OR DEVELOPMENT

This invention was made with government support under HG01182, awarded by the National Institute of Health.

BACKGROUND

Cyanine dyes have been widely used for labeling biomolecules for a variety of applications such as DNA sequencing. See, for example, U.S. Pat. No. 5,571,388, incorporated herein by reference, for exemplary methods of identifying strands of DNA using cyanine dyes. Scientists favor using cyanine dyes in biological applications because, among other reasons, many of these dyes operate in the near IR (NIR) region of the spectrum (600-1000 nm). This makes these cyanine dyes less susceptible to interference from autofluorescence of biomolecules.

Other advantages of cyanine dyes Include: 1) cyanine dyes strongly absorb and fluoresce light; 2) many cyanine dyes do not rapidly bleach under the fluorescence microscope; 3) cyanine dye derivatives can be made that are simple and effective coupling reagents; 4) many structures and synthetic procedures are available and the class of dyes is versatile; and 5) cyanine dyes are relatively small (a typical molecular weight is about 1,000 daltons) so they do not cause appreciable steric interference in a way that might reduce the ability of a labeled biomolecule to reach its binding sight or carry out its function.

Despite their advantages, many of the known cyanine dyes have a number of disadvantages. Some known cyanine dyes are not stable in the presence of certain reagents that are commonly found in bioassays. Such reagents include ammonium hydroxide, dithiothreitol (DTT), primary and secondary amines, and ammonium persulfate (APS). Further, some known cyanine dyes lack the thermal and photostability that is necessary for biological applications such as DNA sequencing and genotyping.

For these reasons, improved, stable cyanine dyes are needed, especially for use in labeling biomolecules.

SUMMARY

The methods, compounds, dyes, and dye-labeled biomolecules of the present invention solve at least some of the problems of the above-described art.

In one aspect of the invention, a compound of the formula (I) is provided:

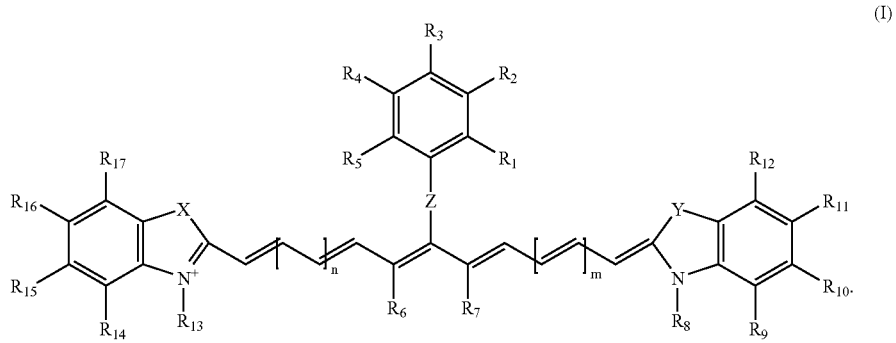

(I)

Z is O, S, or $NR_{35}$ wherein $R_{35}$ is H or alkyl; $R_1$-$R_5$ are each independently H, alkyl, halo, carboxyl, amino, or $SO_3^-Cat^+$, wherein $Cat^+$ is a cation and at least one of $R_1$-$R_5$ is $SO_3^-Cat^+$; $R_8$ and $R_7$ are each H, alkyl, or optionally, together with the group to which they are bonded, form a ring; m and n are each independently integers from 0 to 5; X and Y are each independently O, S, Se, or $CR_{19}R_{20}$, wherein $R_{19}$ and $R_{20}$ are each independently alkyl, or optionally form a ring together with the carbon atom to which they are bonded; $R_8$ and $R_{13}$ are each independently alkyl, $(CH_2)_rR_{25}$ or $(CH_2)_rR_8$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group; and $R_9$-$R_{12}$ and $R_{14}$-$R_{17}$ are each independently H, alkyl, halo, amino, sulfonato, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl, or optionally $R_{11}$ and $R_{12}$ together with the atoms to which they are bonded form an aromatic ring, or optionally $R_{16}$ and $R_{17}$ together with the atoms to which they are bonded form an aromatic ring.

In another aspect of the invention, a compound of the formula (V) is provided:

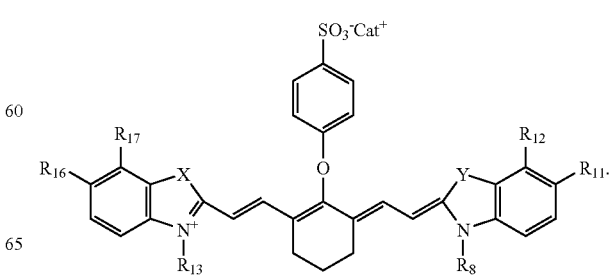

(V)

Cat+ is cation; X and Y are each independently O, S, Se, or (CH$_3$)$_2$C; and R$_8$ and R$_{13}$ are each independently alkyl, (CH$_2$)$_r$R$_{25}$ or (CH$_2$)$_r$R$_{18}$; wherein at least one of R$_8$ and R$_{13}$ is (CH$_2$)$_r$R$_{18}$ and wherein r is an integer from 1 to 20, and R$_{25}$ is a functional group that does not directly react with a carboxyl, hydroxyl, amino, or a thiol group, and R$_{18}$ is a functional group that can react with a carboxyl, hydroxyl, amino, or thiol group; R$_{11}$ and R$_{12}$ are either H, sulfonato, or together with the atoms to which they are bonded form an aromatic ring; and R$_{16}$ and R$_{17}$ are either H, sulfonato, or together with the atoms to which they are bonded form an aromatic ring.

In another aspect of the invention, a method of labeling a biomolecule using a dye of the formula (I) comprises reacting a dye of the formula (I) with the biomolecule. The resulting dye-labeled biomolecule is still another aspect of the invention.

In another aspect of the invention, a method of labeling a biomolecule using a dye of the formula (V) comprises reacting a dye of the formula (V) with the biomolecule. The resulting dye-labeled biomolecule is still another aspect of the invention.

In yet another aspect of the invention, a kit for labeling biomolecules comprises a dye of the formula (I) and a buffer. Similarly, in another aspect of the invention, a kit for labeling biomolecules comprises a dye of the formula (v) and a buffer.

The present invention provides the foregoing and other features, and the advantages of the invention will become further apparent from the following detailed description of the presently preferred embodiments, read in conjunction with the accompanying examples. The detailed description and examples are merely illustrative of the invention and do not limit the scope of the invention, which is defined by the appended claims and equivalents thereof.

DETAILED DESCRIPTION

Definitions

"Alkyl" is a saturated aliphatic group, including substituted and unsubstituted straight-chain alkyl groups, substituted and unsubstituted branched alkyl groups, and substituted and unsubstituted cycoalkyl groups. The term "alkyl" includes alkoxy, haloalkyl, hydroxyalkyl, and alkyloxyalkyl ether species. In preferred embodiments, a straight chain or branched chain alkyl has 50 or fewer carbon atoms In its backbone, more preferably 30 or fewer, and most preferably 10 or fewer. Preferred cycloalkyls have from 3-10 carbon atoms in their ring structure, and more preferably have 3-6 carbon atoms. "Lower alkyl" means an alkyl group having from 1-10 carbon atoms in its backbone, more preferably from 1-6 carbon atoms. Alkyl cyclic groups can be single or polycyclic, containing between 3 to 12 atoms per ring, but preferably between 1 and 9 atoms in the backbone. Preferred substituents on an alkyl backbone include substituted or unsubstituted alkyl radicals, halo, carboxyl, amino, and sulfanato groups.

"Alkenyl" and "alkynyl" are unsaturated aliphatic substituents analogous in length and possible substitution to the alkyl radicals described above, but which contain at least one double or triple bond, respectively.

"Amino" is an —NRR' group where R and R' can be the same or different, and either can be H or alkyl. Preferably, at least one of R and R' is H. Optionally, an additional substituent can be added, making a quaternary ammonium ion.

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aryl groups include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, etc. The aryl group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Biomolecule" is a natural or synthetic molecule for use in biological systems. Preferred biomolecules include a protein, a peptide, an enzyme substrate, a hormone, an antibody, an antigen, a hapten, an avidin, a streptavidin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA.

"Cyanine dye" generically refers to a compound having two substituted or unsubstituted nitrogen-containing heterocyclic rings joined by an unsaturated bridge.

"Linking group" is a moiety capable of reacting with a complementary functionality (preferably, a carboxyl, hydroxyl, thiol, or amino functionality) of a biomolecule, such reaction forming a "linkage" attaching a dye to the biomolecule. See R. Haugland, Molecular Probes Handbook of Fluorescent Probes and Research Chemicals, Molecular probes, Inc. (1992). In this disclosure, R$_{18}$ represents a linking group before the attachment reaction occurs, R$_{30}$ represents the resultant attachment between the dye and the biomolecule. Preferred linking groups include phosphoramidite groups, NHS ester, carboxylic acid, thiocyanate, and isothiocyanate.

"Sulfonato" is an SO$_3^-$ group, optionally bonded to a cation.

"Sulfo-phenoxy dye" is a cyanine dye wherein the unsaturated bridge of the cyanine dye is substituted with an ether linkage to a benzene ring that is substituted with a sulfonato group, preferably in the 4 position on the benzene ring.

All other acronyms and abbreviations have the corresponding meaning as published in journals relative to the art of organic chemistry.

Preferred Cyanine Dyes

A preferred cyanine dye is a compound of the formula (I):

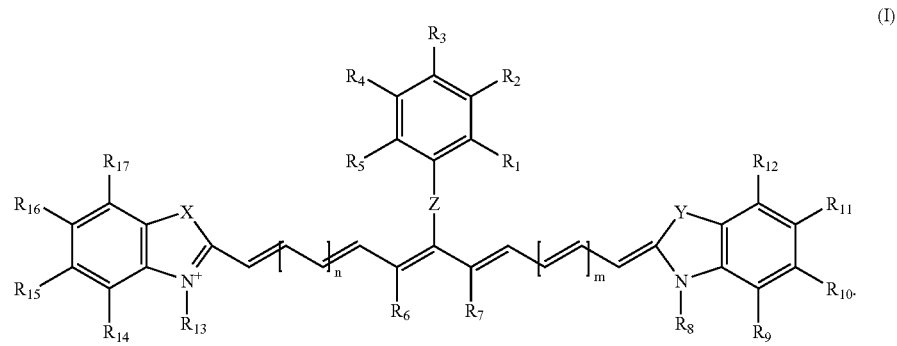

(I)

Preferably, Z is a heteroatom having at least one lone pair of electrons. In a particularly preferred embodiment, Z is O, S, or $NR_{35}$ wherein $R_{35}$ is H or alkyl. If $R_{35}$ is alkyl, it is preferred that $R_{35}$ is lower alkyl. Preferably, Z is of such a structure that only one atom is in the direct linkage between the benzene ring bonded to Z and to the polyene chain of the formula

bonded to Z. Side chains on the linkage between the benzene ring and the polyene chain are acceptable. In those embodiments having side chains, lower alkyl side chains are preferred.

$R_1$-$R_5$ are each independently H, alkyl, halo, carboxyl, amino, or $SO_3^-Cat^+$, wherein $Cat^+$ is a cation and at least one of $R_1$-$R_5$ is $SO_3^-Cat^+$. It is preferred that $R_3$ be $SO_3^-Cat^+$. It is particularly preferred that $Cat^+$ be $H^+$ or an alkali metal ion such as $Na^+$.

$R_6$ and $R_7$ are each H, alkyl, or optionally, together with the

group to which they are bonded, form a ring. It is preferred that $R_6$ and $R_7$ together with the atoms to which they are bonded form a ring. It is preferred that the ring have 4 to 10 member atoms, more preferably 5 or 6 member atoms. In one preferred embodiment, it is preferred that the ring including $R_6$ and $R_7$ be substituted, preferably with a sulfonato radical.

The integers m and n are each independently integers from 0 to 5. Preferably, both the sum of m and n is two. More preferably, the sum of m and n is one. Most preferably, both m and n are zero. As the sum of m and n rises, so too does the wavelength of the dye. Generally, the addition of each double bond in the polyene chain can increase the wavelength by about 40 to 120 nm. For the absorption changes accompanied with trimethine to pentamethine or pentamethine to heptamethine, there is a typically a bathochromic shift (red shift) of about 100 nm. For example, when m and n are both 0, the wavelength of the preferred dye is about 770 nm. When m and n are both 1, the wavelength of the preferred dye is about 950 nm. The most preferred dyes operate in the NIR spectrum (600-1000 nm).

X and Y are each independently O, S, Se, or $CR_{19}R_{20}$, wherein $R_{19}$ and $R_{20}$ are each independently alkyl, or optionally form a ring together with the carbon atom to which they are bonded. It is preferred that X and Y are a heteroatom such as O, S, and Se. When X or Y is $CR_{19}R_{20}$, it is preferred that both $R_{19}$ and $R_{20}$ are both lower alkyl, more preferably, both $R_{19}$ and $R_{20}$ are both methyl.

$R_8$ and $R_{13}$ are each independently alkyl, $(CH_2)_rR_{25}$ or $(CH_2)_rR_{18}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In a preferred embodiment one of $R_8$ and $R_{13}$ is $(CH_2)_rR_{18}$ and the other is $(CH_2)_rR_{25}$. In other words, it is preferred that one of $R_8$ and $R_{13}$ react with the biomolecule to form a bond to that biomolecule, and that the other does not react. The $R_{18}$ group must be able to covalently bond with the biomolecule being labeled. Particularly preferred $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. Particularly preferred $R_{25}$ groups include hydroxyl, thioacetyl, and sulfonato.

$R_9$-$R_2$ and $R_{14}$-$R_{17}$ are each independently H, alkyl, halo, amino, sulfonato, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl or optionally $R_{11}$ and $R_{12}$ together with the atoms to which they are bonded form an aromatic ring, or optionally $R_{16}$ and $R_{17}$ together with the atoms to which they are bonded form an aromatic ring. In one preferred embodiment, one or both of $R_{11}$ and $R_{16}$ is sulfonato. In another preferred embodiment, when $R_{11}$ and $R_{12}$ together with the atoms to which they are bonded form an aromatic ring, the ring is substituted in at least one position with a sulfonato group. In another preferred embodiment, when $R_{16}$ and $R_{17}$ together with the atoms to which they are bonded form an aromatic ring, the ring is substituted in at least one position with a sulfonato group, a halo group, an alkyl substituent, or an amino substituent.

Another preferred cyanine dye is of the formula (V):

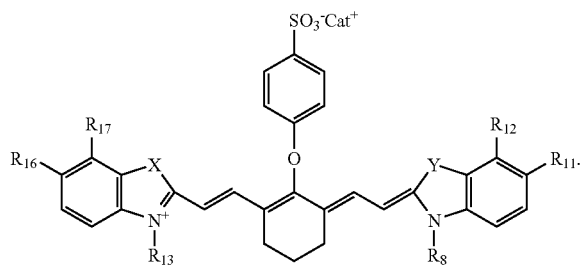

(V)

$Cat^+$ is a cation. Preferably, $Cat^+$ is $H^+$ or a metal ion. More preferably, $Cat^+$ is an alkali metal ion, most preferably $Na^+$. X and Y are each independently O, S, Se, or $(CH_3)_2C$.

$R_8$ and $R_{13}$ are each independently alkyl, $(CH_2)_rR_{25}$ or $(CH_2)_rR_{18}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In a preferred embodiment, one of $R_8$ and $R_{13}$ is $(CH_2)_rR_{18}$ and the other is $(CH_2)_rR_{25}$. In other words, it is preferred that one of $R_8$ and $R_{13}$ react with the biomolecule to form a bond to that biomolecule, and that the other does not react. The $R_{18}$ group must be able to covalently bond with the biomolecule being labeled. Particularly preferred $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. Particularly preferred $R_{25}$ groups include hydroxyl, thioacetyl, and sulfonato.

$R_{11}$ and $R_{12}$ are either H, sulfonato, or together with the atoms to which they are bonded form an aromatic ring. In a preferred embodiment, $R_{11}$ is sulfonato. In another preferred embodiment, when $R_{11}$ and $R_{12}$ together with the atoms to which they are bonded form an aromatic ring, the ring is substituted in at least one position with a sulfonato group.

$R_{16}$ and $R_{17}$ are either H, sulfonato, or together with the atoms to which they are bonded form an aromatic ring. In a preferred embodiment, $R_{16}$ is sulfonato. In another preferred embodiment, when $R_{16}$ and $R_{17}$ together with the atoms to which they are bonded form an aromatic ring, the ring is substituted in at least one position with a sulfonato-group.

The preferred cyanine dyes can be excited efficiently by commercially available equipment purchasable through companies such as Toshiba, Phillips, Blue Sky Research, and NEC.

The preferred cyanine dyes have sufficient solubility in aqueous solutions that once they are attached to a soluble biomolecule, the biomolecule retains its solubility. The preferred dyes also have good solubility in organic media, which provides considerable versatility in synthetic approaches to the labeling of desired biomolecules.

The preferred cyanine dyes have increased chemical stability in the presence of ammonium hydroxide and DTT. The preferred cyanine dyes have improved photostability and thermostability over existing phenoxy cyanine dyes.

Preparing the Preferred Cyanine Dyes

The preferred cyanine dyes are prepared using methods that are well known in the art Generally, cyanine dyes are prepared according to the procedures taught in Hamer, F. M., *Cyanine Dyes and Related Compounds*, Weissberger, M. A., ed. Wiley Interscience, N.Y. 1964. Further, U.S. Pat. Nos. 4,337,063; 4,404,289 and 4,405,711, incorporated herein by reference, describe a synthesis for a variety of cyanine dyes having N-hydroxysuccinimide active ester groups. U.S. Pat. No. 4,981,977, incorporated herein by reference, describes a synthesis for cyanine dyes having carboxylic acid groups. U.S. Pat. No. 5,268,486, incorporated herein by reference, discloses a method for making arylsulfonate cyanine dyes. U.S. Pat. No. 6,027,709, incorporated herein by reference, discloses methods for making cyanine dyes having phosphoramidite groups. U.S. Pat. No. 6,048,982, incorporated herein by reference, discloses methods for making cyanine dyes having a reactive group selected from the group consisting of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

One common synthesis route involves preparing substituted or unsubstituted indolesulfonate quaternary salts according to procedures that are well known in the art, some of which are detailed in the examples of this specification. Particularly preferred indole quaternary salts include, among others, indolesulfonate quaternary salt and benzindole alcohol quaternary salt, which are exemplified in this specification.

The pair of synthesized salts are then reacted with a commercially available (through ALDRICH) Schiffs base such as N-[(3-(Anilinomethylene)-2-chloro-1-cyclohexen-1-yl) methylene]aniline monohydrochloride using techniques and reaction conditions that are well known in the art, some of which are detailed in the examples of this specification. The product is then reacted with a hydroxybenzene sulfonic acid to give a dye according the present invention. The dye can be further modified to give other dyes according to the present invention, for example, by reacting the dye with commercially available phosphoramidites such as 2-cyanoethyl tetraisopropylphosphorodiamidite using techniques and reaction conditions that are well known in the art, some of which are detailed in the examples of this specification.

Labeling Biomolecules

The cyanine dyes of the present invention can be attached to biomolecules, which are defined above. Through (inking groups, the cyanine dye can be linked to the biomolecule, for example, by using phosphoramidite chemistry, ultimately forming a phosphate linkage between the dye and the biomolecule. For examples of such labeling methods, see U.S. Pat. No. 6,027,709, which discloses many preferred linking groups, linking methods, and biomolecules that can be readily labeled. It is generally preferred to prepare a phosphoramidite of a cyanine dye to label DNA molecules in a DNA synthesis machine. It is preferred to attach the dye to the 5' end of a protected, support-bonded oligonucleotide through standard phosphoramidite chemistry. Synthesis at the 200 nmole scale produces typical crude yields of dye labeled oligonucleotides of 50-60 nmole.

Many methods of linking dyes to various types of biomolecules are well known in the art. For a through review of oligonucleotide labeling procedures, see R. Haugland in Excited States of Biopolymers, Steiner ed., Plenum Press (1983), Fluorogenic Probe Design and Synthesis: A Technical Guide, PE Applied Biosystems (1996), and G. T. Herman, Bioconjugate Techniques, Academic Press (1996).

It is preferred that antibody labeling is carried out in a buffer in an organic solvent, under basic pH conditions, and at room temperature. It Is also preferred that the labeled antibody be purified by gel permeation chromatography using equipment such as a SEPHADEX G-50 column to remove unconjugated dye.

In a preferred embodiment method of labeling a biomolecule, the $R_{18}$ group of either the $R_8$ or the $R_{13}$ group of any of the preferred cyanine dyes reacts with a thiol, a hydroxyl, a carboxyl, or an amino group on a biomolecule, forming an attachment ($R_{30}$) between the dye and the biomolecule. Typically, this reaction is carried out in mixtures of aqueous buffer and an organic solvent such as DMF at pH 8 to 9. In one preferred embodiment, using phosphoramidite chemistry, solid phase synthesis is preferred, as disclosed in U.S. Pat. No. 6,027,709.

Biomolecules can be labeled according to the present invention using a kit In a preferred embodiment of a kit, the kit comprises a dye of either formula (I) or (V), and a buffer. Preferably, the kit contains a coupling buffer such as 1 M $KH_2PO_4$ (pH 7.0). Preferably, the buffer has a qualified low fluorescence background.

Optionally, the kit can contain a purification sub-kit. After labeling a biomolecule with one of the preferred dyes, the labeled biomolecule may be separated from any side reaction products and any free hydrolyzed product resulting from normal hydrolysis. For biomolecules containing 13 or fewer amino acids, preparative thin layer chromatography (TLC) can remove impurities. PANVERA supplies a TLC Peptide Purification Kit, which is specially designed to purify dye-labeled peptides or proteins.

For larger biomolecules such as larger peptides or proteins, a SEPHADEX G-15 or G-25 resin may remove unwanted derivatives. PANVERA supplies a Gel Filtration of Proteins Kit, which is designed to separate dye-labeled peptides and proteins from free dye. The dye-labeled biomolecules that remain after desalting can often be used successfully without further purification. In some cases, it may be necessary to resolve and assess the activity of the different dyed products using HPLC or conventional chromatography.

Once labeled, one preferred dye-labeled biomolecule is of the formula (XV):

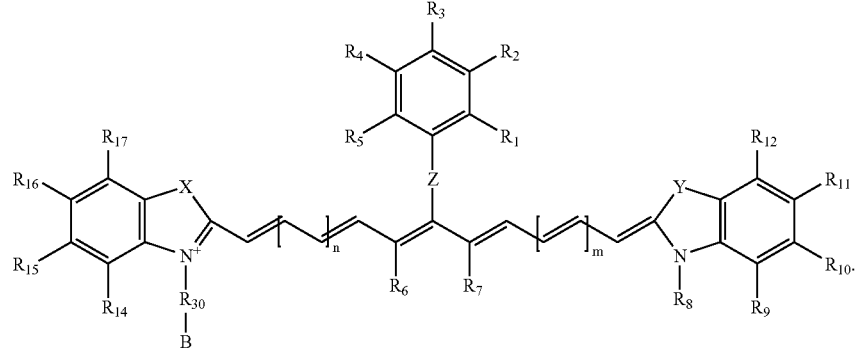

(XV)

All of the substitutents are defined as above. B is a biomolecule and $R_{30}$ is $(CH_2)_rL$ wherein r is an integer from 1 to 50, and L is a linking group. Preferably, B is a protein, a peptide, an enzyme substrate, a hormone, an antibody, an antigen, a hapten, an avidin, a streptavidin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA. For a list of preferred label terminators for use in DNA sequencing, see U.S. Pat. No. 5,332,666, herein incorporated by reference.

Preferably, r ranges from 1 to 5. Preferably, L is phosphoramidityl or other linkage group, some of which are exemplified in U.S. Pat. No. 6,027,709. In one preferred embodiment, L is a diphosphate ester amidite.

Another preferred dye-labeled biomolecule is of the formula (XX):

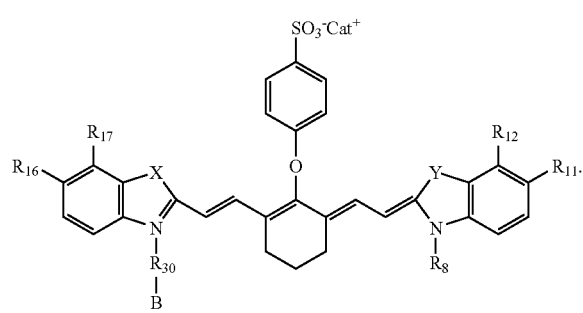

(XX)

All of the substitutents are defined as above. B is a biomolecule and $R_{30}$ is $(CH_2)_rL$ wherein r is an integer from 1 to 50, and L is a linking group. Preferably, r ranges from 1 to 5. In one preferred embodiment, when the linkage is formed, L is a phosphate diester. Examples of similar preferred embodiments are disclosed in U.S. Pat. No. 6,027,709.

DNA Sequencing

The dye-labeled biomolecules of the present invention can be used in biological applications such as DNA sequencing. The labeled biomolecule such as an oligonucleotide can be used, for example, as a primer in the Sanger method of DNA sequencing, as a tailed primer for genotyping or as a hybridizaton probe. Certain well-known techniques and reaction conditions for DNA sequencing are detailed in the examples of this specification.

Well-known methods of DNA sequencing include the Maxam-Gilbert chemical degradation method, described in Maxam et al., Meth. in Enzym. 65:499 (1980), and the Sanger dideoxy chain termination technique, described in Sanger et al., P.N.A.S. USA 74:5463 (1977). In each method DNA fragments labeled with $^{32}P$ are generated which are analyzed by gel electrophoresis. Radio-labeled phosphorus is not commonly used in these methods anymore; dyes have taken its place.

DNA sequencing is also summarized in review articles. See, e.g., Middendorf, L. R., Humphrey, P. G., Narayanan, N., and Roemer, R. C. "Sequencing Technology" in: Biotechnology. Rehm, H.-J. and Reed, G. (Editors), Wiley-VCH Publishers, Germany—(Chapter-submitted); B: Barrell, The FASEB Journal, 5, 40 (1991); and G. L. Trainor, Anal. Chem. 62, 418 (1990), and references cited therein. The most widely used DNA sequencing chemistry is the enzymatic chain termination method of Sanger, mentioned above, which has been adopted for several different sequencing strategies. The sequencing reactions are either performed in solution with the use of different DNA polymerases, such as the thermophilic Taq DNA polymerase [M. A. Innes, Proc. Natl. Acad. Sci. USA, 85: 9436 (1988)] or specially modified T7 DNA polymerase ("SEQUENASE") [S. Tabor and C. C. Richardson, Proc. Natl. Acad. Sci. USA, 84, 4767 (1987)], or in conjunction with the use of polymer supports. See for example S. Stahl et al., Nucleic Acids Res., 16, 3025 (1988); M. Uhlen, PCT Application WO 89/09282; Cocuzza et al., PCT Application WO 91/11533; and Jones et al., PCT Application WO 92/03575, incorporated by reference herein.

EXAMPLES

The following section shows one of the preferred syntheses for making various compounds made according to the present invention, as well as experimental data for particular compounds. This section also provides examples for using the compounds made according to the present invention. The examples are intended to be illustrative, not limiting.

Example 1

Synthesizing an Intermediate Cyanine Dye

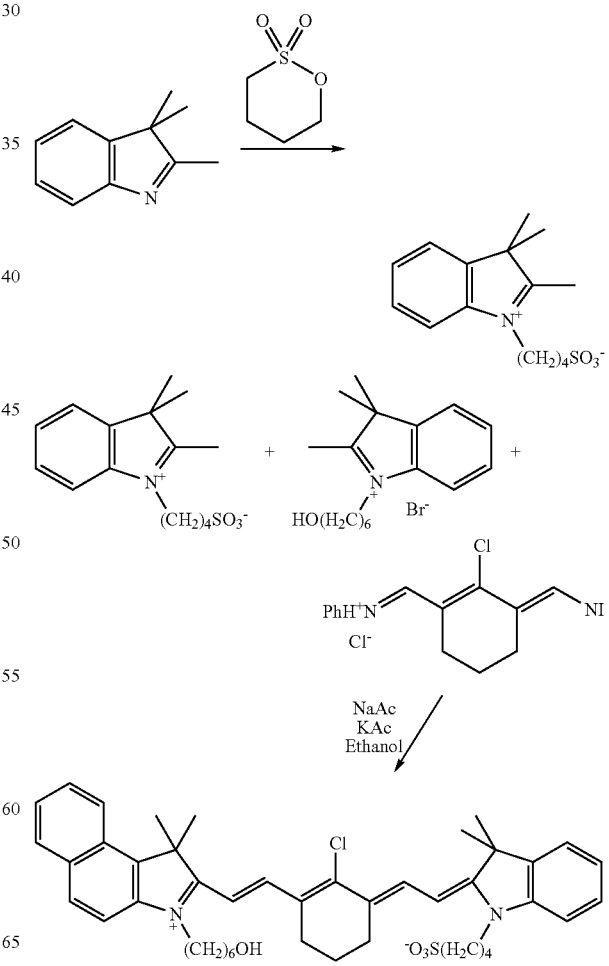

Step A: synthesis of indolesulfonate quaternary salt. A mixture of 160 g (1000 mmol) of 1,1,2-trimethyl-1H-indole (ALDRICH) and 340.4 g (256 ml; 2500 mmol; ALDRICH) of butanesultone was heated at 125° C. in 1L RB flask with 400 ml of dichlorobenzene under the nitrogen atmosphere. After 16 h, the reaction was stopped and cooled to room temperature. The solid crystallizing out of the reaction mixture was filtered, then washed with ether (150 ml). The solid so obtained was dissolved in minimum volume of methanol (300 ml) and then precipitated by the addition of acetone (1600 ml). The solid was filtered and washed with acetone (150 ml×2). It was dried under vacuum to give 261.3 g (88.5%) of the quaternary salt. It was pure enough to use for the next step.

Step B: synthesis of benzindole alcohol quaternary salt: The quaternary salt was prepared according to the procedure of U.S. Pat. No. 6,027,709. In this case, 92.0 g of 1,1,2-Trimethyl-1H-benzindole (ACROS) was used, giving 113.0 g (60% yield) of pure benzindole alcohol quaternary salt.

Step C: synthesis of IRD 800-chloro dye: A mixture containing benzindole alcohol quaternary salt (39 g; 100 mmol), indolesulfonate quaternary salt (20.5 g; 100 mmol), in ethanol (400 ml) was stirred under nitrogen for 10 to 15 min. to obtain the uniform solution. To this solution was then added Schiffs base (35.9 g; 100 mmol; ALDRICH) followed by the addition of 100 ml of ethanol. The dark red colored solution was heated to 60° C. At this temperature, sodium acetate (21.32 g; 130 mmol) was added, followed by 12.80 g of potassium acetate (130 mmol). Temperature was raised to obtain vigorous reflux (110 to 115° C.) and maintained at this reflux for 35 to 40 min. Reaction was stopped and cooled to room temperature. The reaction mixture was poured into an ice bath (1L) when an oily product formed and settled to the bottom. Water was decanted and the procedure was repeated until the water washings were clear. The oily product was triturated with ether (150 ml×3) and then with ethyl acetate (150 ml×3). The partially solidified product was dissolved in methanol (350 ml) and methanol was subsequently removed by evaporation on rotary evaporator. The solid dye was dried under vacuum. It was further purified by column chromatography (silica gel 60, 35-75 mm; solvent gradient 10% methanol in acetonitrile to 30% methanol in acetonitrile) to give a pure chloro dye (29.0 g; Yield 40%).

Example 2

Synthesizing a Cyanine Dye

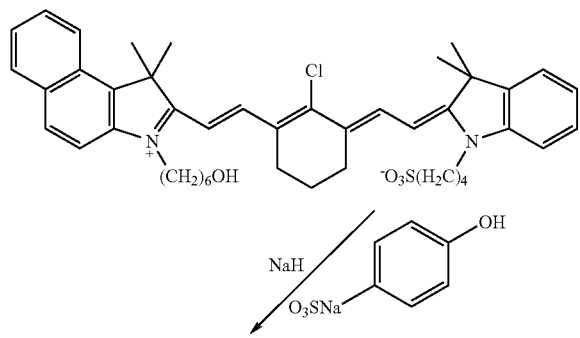

-continued

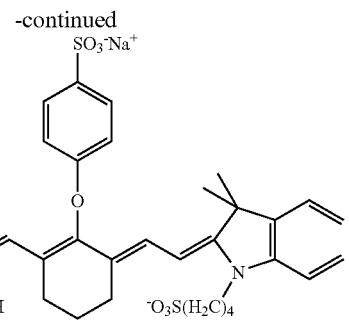

Synthesis of sulfo-phenoxy dye: In 40 ml of dry DMF was dissolved 2.95 g (12.70 mmol) of 4-hydroxybenzenesulfonic acid. After adding 1.08 g (60%; 26.8 mmol) of sodium hydride, the mix was stirred at room temperature for 10 min. under nitrogen. IRD-800-chloro dye (7.41 g; 10 mmol), dissolved in 25 ml of dry DMF was added to the reaction mixture and stirred further for 45 to 50 min. Absorption max of 788 nm at the end of this period Indicated an hypsochromic shift of 13 nm (chloro dye abs. at 801 nm), and thus the formation of the sulfo-phenoxy dye. Dry ice was added to the reaction mixture and DMF was removed under vacuum. The crude dye was purified by column chromatography (silica gel 60; solvent gradient: 10% methanol in acetonitrile to 30% methanol in acetonitrile) to obtain 4 g of the pure dye. (Yield 45%).

Example 3

Synthesizing a Sulfo-Phenoxy Phosphoramidite Cyanine Dye

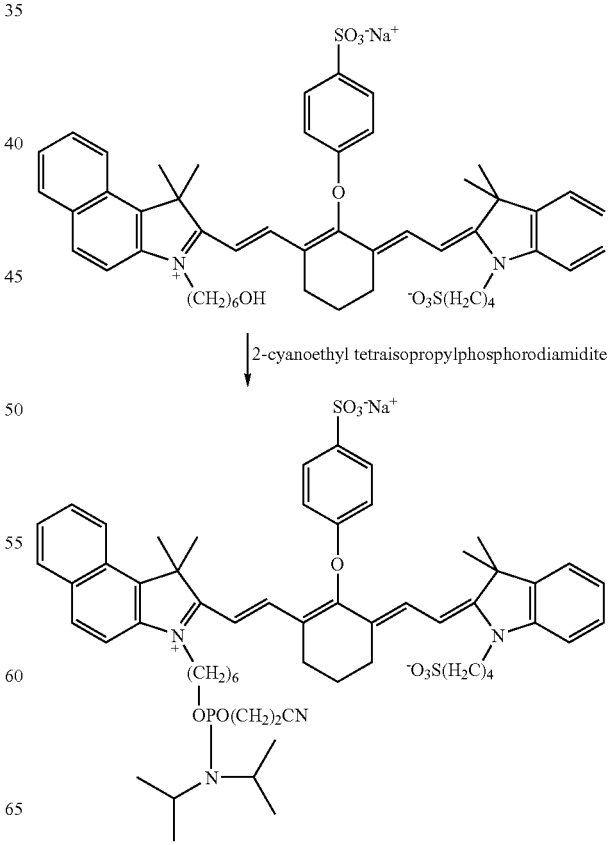

Synthesis of a sulfo-phenoxy dye: In 20 ml of dry methylene chloride was dissolved 1.4 g (1.59 mmol) of the above sulfo-phenoxy dye and the solution was cooled in an ice-acetone bath with stirring under nitrogen. After adding 0.6 g (1.01 ml; 3.18 mmol) of 2-cyanoethyl tetraisopropylphosphorodiamidite, and 0.045 g (1.3 ml; 0.64 mmol) of 1-H tetrazole solution (0.5M) at 0° C., the solution was stirred at room temperature for 2 to 2.5 h. Methylene chloride that contained 1% triethyl amine was added to the reaction mixture the reaction mixture was then subjected to washings with 5% sodium bicarbonate (50 ml×2) and water (50 ml×2). After drying over anhydrous sodium sulfate, the solution was filtered and the filtrate was concentrated to 5 ml. The concentrated solution was added at 0° C. to hexane (50 ml) under stirring and under nitrogen. The viscous residue obtained after the decantation of hexane was triturated with ether (50 ml) to give solid powder. It was dried under vacuum to give green powder of sulfo-phenoxy phosphoramidite (1.0 g; Yield 58%).

Example 4

Synthesizing an Intermediate Cyanine Dye

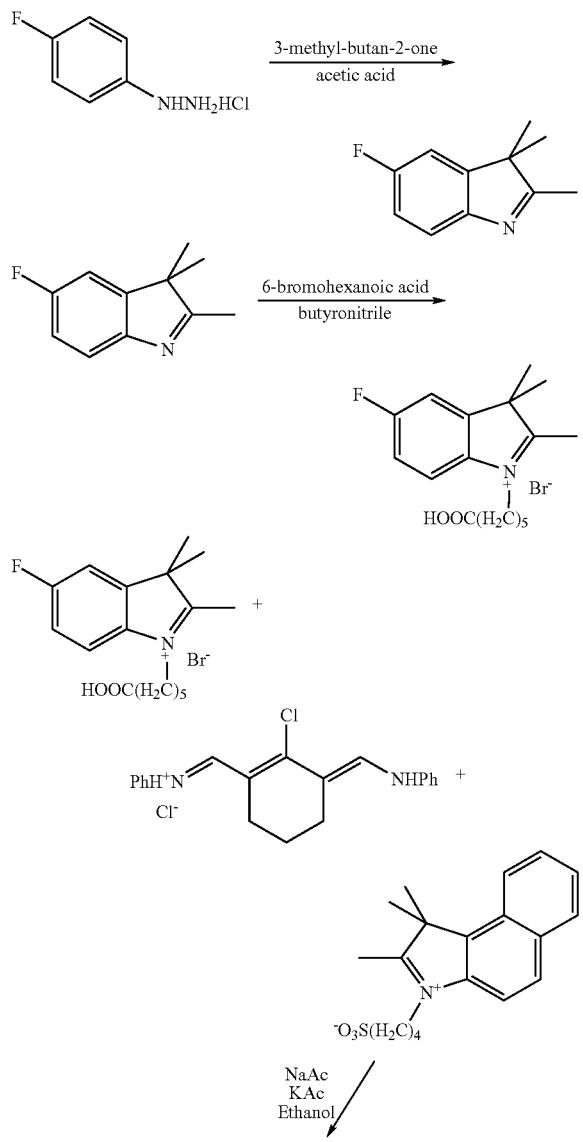

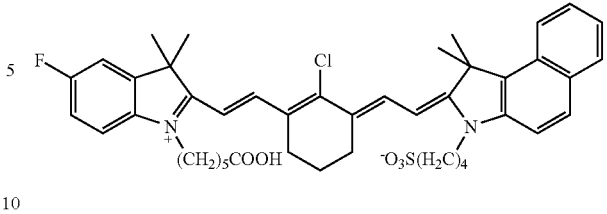

Step A: synthesis of 5-fluoro indole: A mixture containing 4-Fluorophenylhydrazine hydrochloride (5.0 g; 30.75 mmol; ALDRICH), 3-methyl-2-butanone (3.7 g; 43 mmol; ALDRICH) and acetic acid (30 ml) was stirred for 30 min. under nitrogen to obtain the clear solution. The mixture was then refluxed at 130° C. The appearance of UV-Vis Abs. Max at 255 nm and the disappearance of the peak at 282 nm confirmed the formation of the indole. At the end of 40 min. the reaction was stopped and the mixture was poured into crushed ice (100 g). The residue was extracted into ethyl acetate (100 ml×2), washed with water (100 ml×2) and ethyl acetate layer was dried over anhydrous sodium sulfate. After filtration, ethyl acetate was removed, and the residue was dried to give 4.15 g of the indole (Yield 76%).

Step B: synthesis of 5-fluoroindole carboxylate salt: A mixture containing 5-Fluoroindole (3.0 g; 16.9 mmol), 6-bromohexanoic acid (5.38 g; 27.6 mmol; ALDRICH), in butyronitrile 90 ml was refluxed under nitrogen at 140-145° C. The quaternization was complete after 35 to 40 h. The reaction mixture was cooled to room temperature and triturated with ether and finally dried under vacuum to give the solid (6.0 g; Yield 95%).

Step C: synthesis of benzindolesulfonate quaternary salt: This salt was prepared according to the procedure outlined for synthesizing indolesulfonate quaternary salt as described in Step A of Example 1.

Step D: synthesis of chloro dye: The product of step C was converted into a chloro dye using the procedure outlined in Step C of Example 1. In this case, 0.4 g (1 mmol) of 5-fluoroindole carboxylate salt and 0.35 g (1 mmol) of benzindole sulfonato were used to obtain 0.27 g (35% yield) of the chloro dye.

Example 5

Synthesizing a Cyanine Dye

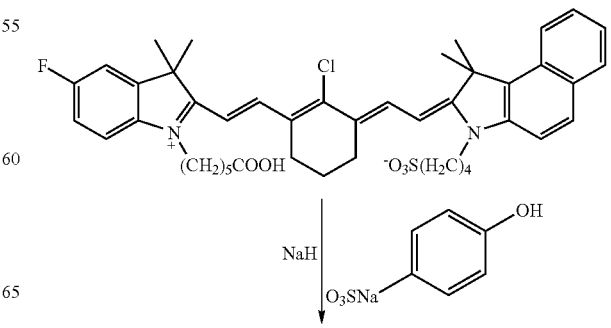

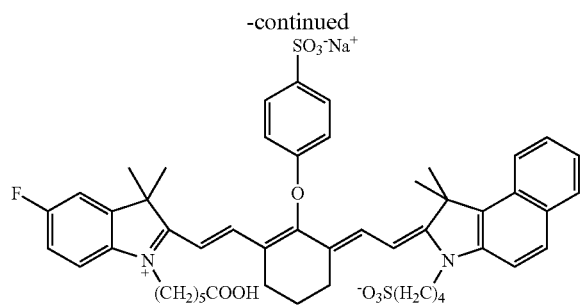

Synthesis of unsymmetrical sulfo-phenoxy dye: The chloro dye of Example 4 was converted into a sulfo-phenoxy dye using the procedure outlined in Example 2. Using 0.7 g (0.91 mmol) of the chloro dye, 0.4 g (48% yield) of the pure sulfo-phenoxy dye was obtained.

Example 6

Synthesizing an NHS Ester Cyanine Dye

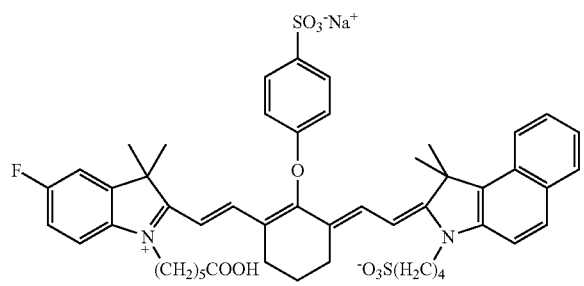

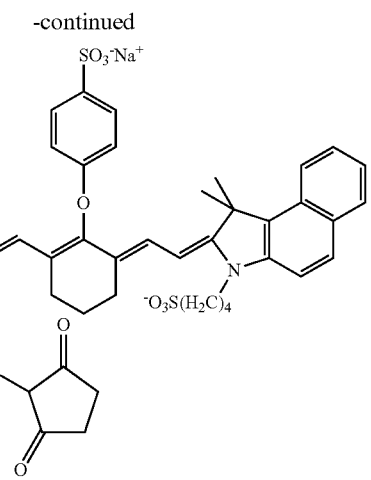

Synthesis of NHS ester dye: Carboxyalkyl dye (0.27 g; 0.3 mmol) that contained 5-fluoroindole and central sulfo-phenoxy group, was dissolved in a mixture of dry DMF (3.0 ml) and dry pyridine (0.3 ml). Disuccinimidyl carbonate (DSC, ALDRICH, 0.115 g; 0.44 mmol) was added and the mixture was stirred at 60° C. for 2 h. under nitrogen. After diluting the mixture with ether (15 ml), and decanting the supernatant, the product was redissolved in dry DMF (2 ml). Ether (15 ml) was added dropwise under stirring to give the solid precipitate. It was filtered, dried under vacuum to give 0.25 g of the reactive dye. (Yield 84%). The formation of the active ester was confirmed by HPLC.

Example 7

Synthesizing a Cyanine Dye

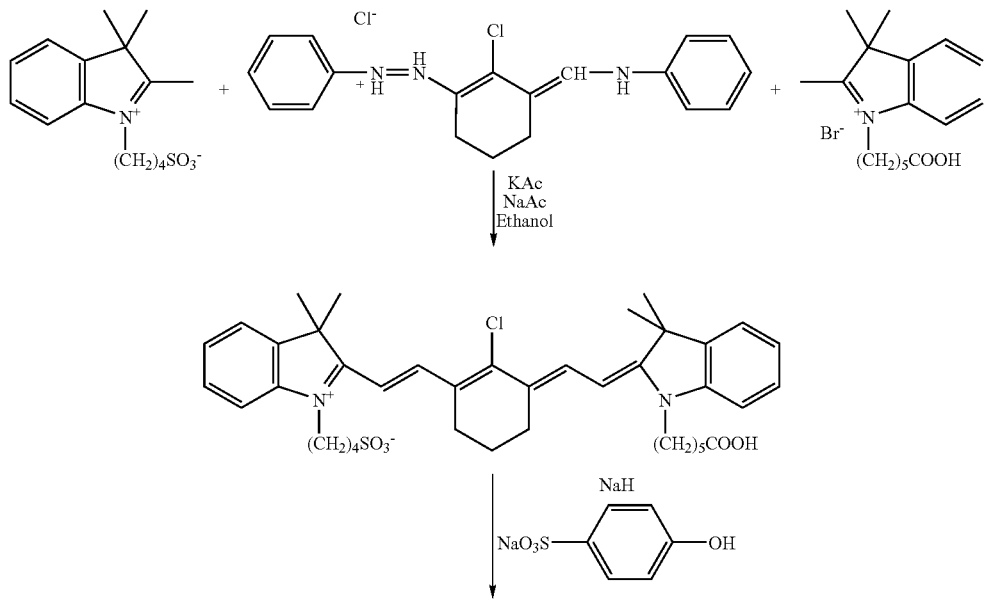

-continued

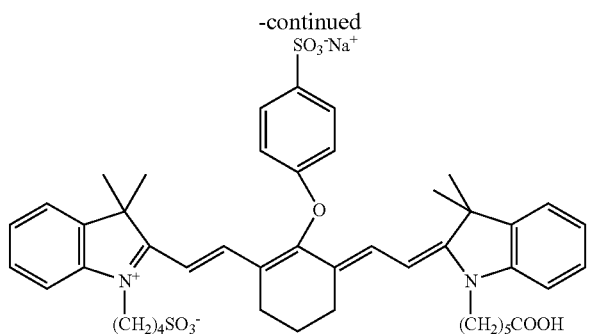

Step A: synthesis of 1-(4-sulfonatobutyl)-2,3,3-trimethylindolinine quaternary salt: A mixture of 1,2,3-trimethylindolenine (15.9 g, 100 mmol) and 1,4-butanesultone (27.2 g, 200 mmol) were heated to 140° C. in 250 ml of 1,2-dichlorobenzene for 16 h. The resulting gummy residue, separated by decanting the solvent was dissolved in minimum amount of methanol and precipitated with acetone. The pink precipitate was filtered and dried under vacuum. Yield: 85%

Step B: synthesis of 1-(6-carboxypentyl)-2,3,3-trimethylindolenine quaternary salt: A mixture of 1,2,3-trimethylindolenine (8 g, 50 mmol) and 6-bromohexanoic acid (19 g, 100 mmol) were heated to reflux in 250 ml of butyronitrile for 36 h. The resulting gummy residue, obtained after solvent removal by rotovap was dissolved in minimum amount of chloroform and precipitated with ether. The precipitate was triturated with ether to get a free flowing dry power. Yield: 70%

Step C: synthesis of chloro dye: A mixture of 5 mmol of each quaternary salts from Step A and Step B along with N-[(3-anilinoethylene)-2-chloro-1-cyclohexen-1-yl)-methylene]aniline monohydrochloride (1.30 g, 5 mmol), sodium acetate (1.1 g, 13 mmol) was refluxed in 30 ml of dry ethanol for 1 h. The reaction mixture was cooled down to remove ethanol by rotovap. The residue was chromatographed on a C18 reversed phase silica gel column (methanol-water, 3:2) to obtain 30% of the desired chloro dye.

Step D: synthesis of sulfo-phenoxy dye: A solution of disodium salt of 4-hydroxybenzene sulfonic acid was prepared as follows: To a suspension of 60% sodium hydride (120 mg, 3 mmol of 100% NaH) in 10 ml of dry DMF, cooled to 0° C. under nitrogen was added a DMF solution (10 ml) of 4-hydroxy benzene sulfonic acid dihydrate, (2 mmol, ALDRICH). After 10 min. the reaction contents were warmed to room temperature for 20 min. Then, the contents were transferred to a flask containing 1 mmol of the chloro dye in 30 ml of DMF with vigorous stirring at room temperature. The reaction was monitored by UV-Vis absorption spectrum that showed a hypsochromic shift from 782 nm to 769 nm. After 30 min., the reaction was quenched with dry ice. DMF was evaporated on a rotovap. Precipitation with ether furnished the crude product as a dry powder that was further purified by reversed phase C18 silica by gel column using 40% aq. methanol. Yield 75%. The pure product was characterized by proton NMR.

Step E: synthesis of NHS ester of the sulfo-phenoxy dye: 2.6 mg of the sulfo-phenoxy dye (0.0031 mmol) was dissolved in 250 μL of dry DMF in a 1.5 ml micro centrifuge tube, to which was added 4.5 mg of N-hydroxysuccinimide (0.039 mmol, ALDRICH) and 10 mg of DCC (0.05 mmol, ALDRICH). The mixture was stirred at room temperature for 16 h and the progress of the reaction was monitored by HPLC. The excess reagents were removed by precipitation with ether and crude dye-N HSE was collected by centrifuging the precipitate, which was further purified by HPLC RPC18 prep column (INERTSIL, ODS 3.5μ, 250×4.6 mm). It was eluted with a solvent gradient of buffer AB 90-10% to buffer 100% B (A=4% acetonitrile in 0.1M TEEAc and B=80% acetonitrile in 0.1 M TEEAc). The fractions were pooled together and the solvent was removed by speed vac. to furnish 2 mg of pure ester. The presence of NHS ester was confirmed by HPLC.

Example 8

Synthesizing an NHS Ester Cyanine Dye

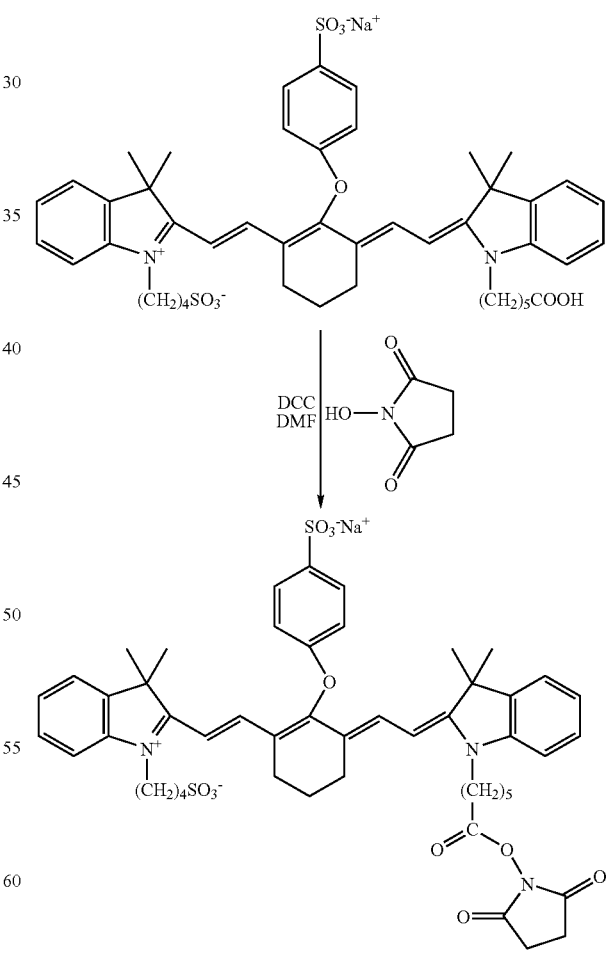

Synthesis of NHS ester dye: The carboxyalkyl dye of Example 7 (2.6 mg; 0.0031 mmol) was dissolved in dry DMF (250 μl). To this solution was added N-hydroxysuccinimide (ALDRICH; 4.5 mg; 0.039 mmol) and dicyclohexylcarbodiimide (DCC; ALDRICH; 10 mg; 0.05 mmol). The mixture was stirred at room temperature for 16 h. The reaction was monitored by HPLC and the NHS ester was purified by passing through RP column (INERTSIL, ODS 3.5μ, 250×4.6 mm) and eluting with a solvent gradient ranging from 10% b (a=4% acetonitrile in 0.1M triethylammonium acetate; b=80% acetonitrile in 0.1M in triethylammonium acetate) to 100% a. The solvent was removed under vacuum to give 2 mg of the pure NHS ester. The presence of reactive NHS ester group was confirmed by HPLC.

Example 9

Synthesizing a Dye-Labeled Acyclo-UTP

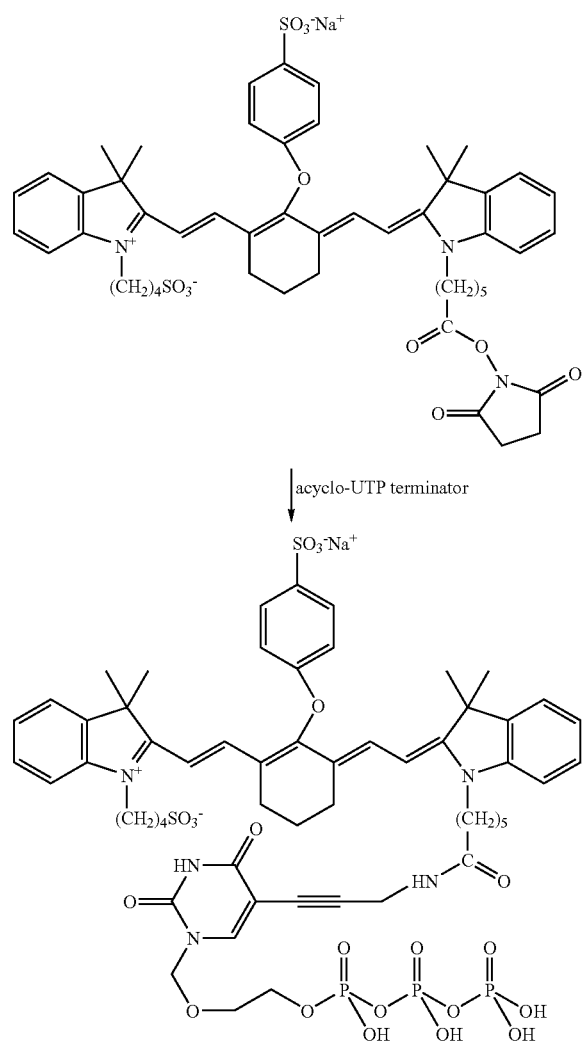

The dye of Example 8 was successfully conjugated to acyclo-terminators-ATP, GTP, CTP and UTP. These unlabeled terminators were obtained from NEN LIFE SCIENCE PRODUCTS, INC. Boston, Mass. The dye labeled terminators were purified in >95% purity by HPLC. Their concentrations were determined by UV-visible absorption spectra obtained in aqueous phosphate buffer. The labeled analogs were used in DNA sequencing and a high quality sequence ladder was obtained with the dye incorporated analogs. The dye labeled-Acyclo-UTP is illustrated above.

Example 10

Labeling DNA

The phosphoramidite of the sulfo-phenoxy dye of Example 2 was used to label DNA molecules prepared in a DNA synthesis machine. The dye was attached to the 5' end of the protected, support-bonded oligonucleotide via phosphoramidite deprotection chemistry. On syntheses at 200 nmol scale typical crude yields of phenoxy dye labeled oligonucleotides are 65 to 95 nmol. The sulfo-phenoxy dye-labeled oligoucleotides were obtained in 100 to 125 nmol.

Example 11

Stability of Sulfo-Phenoxy Dye in $NH_4OH$ & Dithiothreitol (DTT)

The sulfo-phenoxy dye of Example 2 and a counterpart phenoxy dye (200 nmol of ea.) were treated with 400 μl concentrated ammonium hydroxide and incubated at room temperature for 1 h. Another lot of 400 μl of concentrated ammonium hydroxide was added and stirred for additional 0.5 h. These are the conditions that are used in the deprotection of the dye-labeled primers. The reaction was followed at the interval of 15 min. by TLC. In case of phenoxy dye, the formation of the blue-colored impurity was noticed the end of 15 min. The intensity of this impurity increased as the time progressed. After 1.5 h, almost half of the dye was decomposed to give a blue dye. The blue spot was isolated and subjected to absorption and emission. The blue colored impurity gave absorption maximum at 655 nm and emission at 747 nm. Under identical conditions, the sulfo-phenoxy dye did not form any blue colored spot that could be spotted by TLC or absorption.

To study the effect of DTT, 200 nmol dyes were treated with 400 μl of DTT in acetonitrile and stirred at room temperature. After stirring overnight (16 h), TLC indicated the formation of new spots. They were isolated and subjected to absorption. The three spots absorbed at 786 nm, 738 nm and 392 nm respectively. The absorption at 737 nm indicates the formation of new dye due to the decomposition of phenoxy dye that absorbs at 787 nm. Distinct impurity spot made its appearance only after 7 to 8 h. Under identical conditions, sulfo-phenoxy dye did not yield any spot that absorbs at 738 nm.

Both the dyes (phenoxy and sulfo-phenoxy) did not show much variation in their properties such as absorption maximum and extinction coefficient. However, the sulfo-phenoxy dye emits at 828 nm, giving better separation from the absorption maximum of 788 nm. Thus a higher Stoke's shift (40 nm) is obtained with sulfo-phenoxy dye than the phenoxy dye where Stoke's shift value corresponds to 25 nm. This data shows the stability of sulfo-phenoxy dye over its counterpart phenoxy dye.

Scope

It is intended that the foregoing detailed description, including its examples, be regarded as illustrative rather than limiting, and that it be understood that the following claims, including all equivalents, are intended to define the scope of this invention.

What is claimed is:

1. A dye-labeled biomolecule of formula (XV)

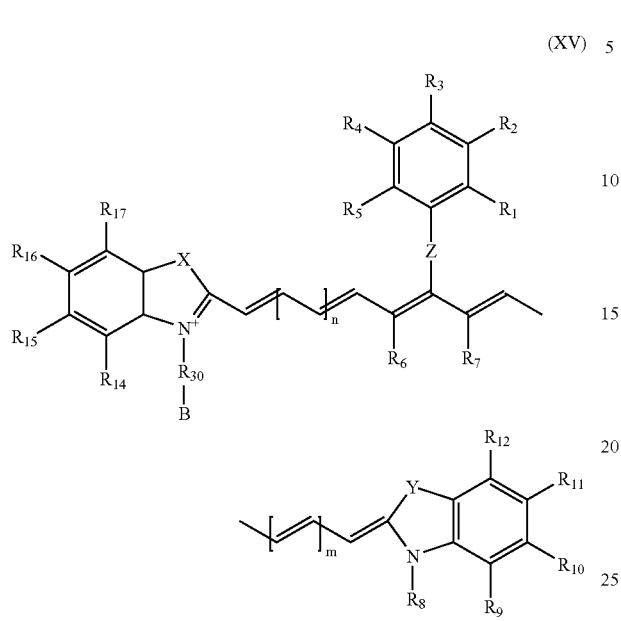

wherein Z is O, S, or $NR_{35}$ wherein $R_{35}$ is H or alkyl;
$R_1$-$R_5$ are each independently H, alkyl, halo, carboxyl, amino, or $SO_3^-Cat^+$, wherein $Cat^+$ is a cation and at least one of $R_1$-$R_5$ is $SO_3^-Cat^+$;
$R_6$ and $R_7$ are each H, alkyl, or optionally, together with the

group to which they are bonded, form a ring;
m and n are each independently integers from 0 to 5;
X and Y are each independently $CR_{19}R_{20}$, wherein $R_{19}$ and $R_{20}$ are each independently alkyl, or optionally form a ring together with the carbon atom to which they are bonded;
$R_8$ is a member selected from the group consisting of alkyl, $(CH_2)_r$, $R_{25}$, $(CH_2)_rR_{18}$, and $R_{30}$—B, wherein r is an integer from 1 to 50, and $R_{25}$ is selected from the group consisting of hydroxyl, thioacetyl, sulfonato, and $R_{18}$ is selected from the group consisting of mercapto, amino, haloalkyl, phosporamidityl, N-hydroxy succinimidyl ester, sulfo N-hydroxy succinimidyl ester, isothiocyanato, iodoacetamidyl, and maleimidyl; and
$R_9$-$R_{12}$ and $R_{14}$-$R_{17}$ are each independently H, alkyl, halo, amino, sulfonato, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl, or optionally $R_{11}$ and $R_{12}$ together with the atoms to which they are bonded form an aromatic ring, or optionally $R_{16}$ and $R_{17}$ together with the atoms to which they are bonded form an aromatic ring;
B is a biomolecule; and
$R_{30}$ is $(CH_2)_rL$; wherein r is an integer from 1 to 50, and L is a linking group.

2. The dye-labeled biomolecule of claim 1, wherein
Z is O;
$R_1$-$R_5$ are each independently H, alkyl, halo, carboxyl, amino, or $SO_3^-Cat^+$, wherein $Cat^+$ is a cation and at least one of $R_1$-$R_5$ is $SO_3^-Cat^+$;
$R_6$ and $R_7$ are each H, alkyl, or optionally, together with the

group to which they are bonded, form a ring;
m and n are each independently integers from 0 to 5;
X and Y are $CR_{19}R_{20}$, wherein $R_{19}$ and $R_{20}$ are each independently alkyl, or optionally form a ring together with the carbon atom to which they are bonded;
$R_8$ is a member selected from the group consisting of alkyl, $(CH_2)_r$, $R_{25}$, $(CH_2)_rR_{18}$, and $R_{30}$—B; wherein r is an integer from 1 to 50, and $R_{25}$ is a functional group consisting of hydroxyl, thioacetyl, sulfonato, and $R_{18}$ is selected from the group consisting of mercapto, amino, haloalkyl, phosporamidityl, N-hydroxy succinimidyl ester, sulfo N-hydroxy succinimidyl ester, isothiocyanato, iodoacetamidyl, and maleimidyl and
$R_9$-$R_{12}$ and $R_{14}$-$R_{17}$ are each independently H, alkyl, halo, amino, sulfonato, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl, or optionally $R_{11}$ and $R_{12}$ together with the atoms to which they are bonded form an aromatic ring, or optionally $R_{16}$ and $R_{17}$ together with the atoms to which they are bonded form an aromatic ring;
B is a biomolecule; and
$R_{30}$ is $(CH_2)_rL$; wherein r is an integer from 1 to 50, and L is a linking group.

3. The dye-labeled biomolecule of claim 1, wherein $R_3$ is $SO_3^-Cat^+$.

4. The dye-labeled biomolecule of claim 3, wherein $Cat^+$ is $H^+$.

5. The dye-labeled biomolecule of claim 3, wherein $Cat^+$ is a metal ion.

6. The dye-labeled biomolecule of claim 5, wherein $Cat^+$ is an alkali metal ion.

7. The dye-labeled biomolecule of claim 1, wherein $R_6$ and $R_7$ are lower alkyl.

8. The dye-labeled biomolecule of claim 1, wherein $R_6$ and $R_7$, together with the

group to which they are bonded, form a ring, said ring being optionally substituted.

9. The dye-labeled biomolecule of claim 8, wherein the ring that includes $R_6$ and $R_7$ is substituted with sulfonate.

10. The dye-labeled biomolecule of claim 8, wherein the ring that includes $R_6$ and $R_7$ has 4 to 10 members.

11. The dye-labeled biomolecule of claim 8, wherein the ring that includes $R_6$ and $R_7$ has 5 or 6 members.

12. The dye-labeled biomolecule of claim 8, wherein the ring that includes $R_6$ and $R_7$ contains a heteroatom.

13. The dye-labeled biomolecule of claim 8, wherein the ring that includes $R_6$ and $R_7$ is substituted in at least one position with an alkyl, amino, or a sulfonate group.

14. The dye-labeled biomolecule of claim 1, wherein m and n are both 0.

15. The dye-labeled biomolecule of claim 1, wherein the sum of m+n is less than 3.

16. The dye-labeled biomolecule of claim 1, wherein at least one of $R_{19}$ and $R_{20}$ is lower alkyl.

17. The dye-labeled biomolecule of claim 16, wherein both $R_{19}$ and $R_{20}$ are methyl.

18. The dye-labeled biomolecule of claim 1, wherein $R_8$ is $(CH_2)_rR_{25}$ and wherein $R_{25}$ is thioacetyl or sulfonato.

19. The dye-labeled biomolecule of claim 1, wherein r is an integer from 1 to 5.

20. The dye-labeled biomolecule of claim 1, wherein $R_9$-$R_{12}$ are each H.

21. The dye-labeled biomolecule of claim 1, wherein one of $R_9$-$R_{12}$ is sulfonato.

22. The dye-labeled biomolecule of claim 1, wherein $R_{14}$-$R_{17}$ are each H.

23. The dye-labeled biomolecule of claim 1, wherein one of $R_{14}$-$R_{17}$ is sulfonato.

24. The dye-labeled biomolecule of claim 1, wherein the biomolecule is selected from the group consisting of a protein, a peptide, an enzyme substrate, a hormone, an antibody, an antigen, an hapten, an avidin, a streptavidin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA.

25. The dye-labeled biomolecule of claim 1, wherein at least one of $R_9$-$R_{12}$ is alkyl, halo, amino, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl.

26. The dye-labeled biomolecule of claim 1, wherein at least one of $R_{14}$-$R_{17}$ is alkyl, halo, amino, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl.

27. A dye-labeled biomolecule of formula

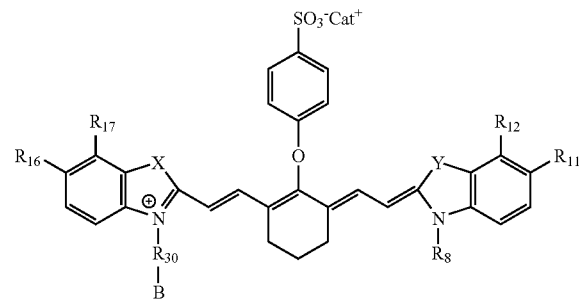

wherein $Cat^+$ is a cation;
X and Y are each $(CH_3)_2C$; and
$R_8$ is a member selected from the group consisting of alkyl, $(CH_2)_r$ $R_{25}$, $(CH_2)_rR_{18}$ and $R_{30}$—B; wherein r is an integer from 1 to 50, and $R_{25}$ is a member selected from the group consisting of hydroxyl, thioacetyl, sulfonato, and $R_{18}$ is selected from the group consisting of mercapto, amino, haloalkyl, phosporamidityl, N-hydroxy succinimidyl ester, sulfo N-hydroxy succinimidyl ester, isothiocyanato, iodoacetamidyl, and maleimidyl, $R_{11}$ and $R_{12}$ are either H, sulfonato, or together with the atoms to which they are bonded form an aromatic ring;

$R_{16}$ and $R_{17}$ are either H, sulfonato, or together with the atoms to which they are bonded form an aromatic ring;

B is a biomolecule; and $R_{30}$ is $(CH_2)_rL$; wherein r is an integer from 1 to 50, and L is a linking group.

28. The dye-labeled biomolecule of claim 27, wherein $Cat^+$ is $H^+$ or a metal ion.

29. The dye-labeled biomolecule of claim 27, wherein r is an integer from 1 to 5.

30. The dye-labeled biomolecule of claim 27, wherein $R_8$ is $(CH_2)_rR_{18}$.

31. The dye-labeled biomolecule of claim 1, wherein the compound has the structure of:

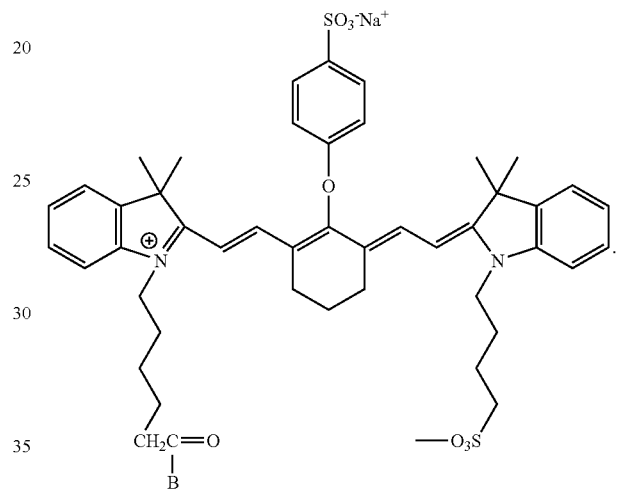

32. The dye-labeled biomolecule of claim 27, wherein $R_8$ is $(CH_2)_rR_{25}$; and
$R_{11}$ and $R_{16}$ are each sulfonato.

33. The dye-labeled biomolecule of claim 27, wherein the biomolecule is selected from the group consisting of a protein, a peptide, an enzyme substrate, a hormone, an antibody, an antigen, an hapten, an avidin, a streptavidin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA.

34. The dye-labeled biomolecule of claim 32, wherein said biomolecule is a carbohydrate.

* * * * *